United States Patent [19]

Smith

[11] Patent Number: 4,863,447
[45] Date of Patent: Sep. 5, 1989

[54] VALVED VENT ASSEMBLY FOR A BODY COLLECTION POUCH

[76] Inventor: Harry C. Smith, 3919 A Potomac, St. Louis, Mo. 63116

[21] Appl. No.: 204,269

[22] Filed: Jun. 9, 1988

[51] Int. Cl.$^4$ ............................................... A61F 5/44
[52] U.S. Cl. ................................ 604/335; 604/324; 251/323; 251/339
[58] Field of Search ............................ 604/332–345, 604/324; 251/128, 321, 322, 323, 337, 339

[56] References Cited

U.S. PATENT DOCUMENTS

| | | | |
|---|---|---|---|
| 688,705 | 12/1901 | Shainwald, Jr. | 251/322 |
| 1,198,956 | 9/1916 | Richardson et al. | 251/323 |
| 2,054,535 | 9/1936 | Diack | 604/333 |
| 2,154,202 | 4/1939 | Gricks | 604/343 |
| 3,216,420 | 11/1965 | Smith et al. | 604/339 |
| 3,865,109 | 2/1975 | Elmore et al. | 128/283 |
| 3,998,255 | 12/1976 | Mather et al. | 150/1 |
| 4,014,365 | 3/1977 | Peterson et al. | 251/339 |
| 4,211,224 | 7/1980 | Kubach et al. | 604/333 |
| 4,232,672 | 11/1980 | Steer et al. | 604/333 |
| 4,366,836 | 1/1983 | Villari | 604/324 |
| 4,411,659 | 10/1983 | Jensen et al. | 604/332 |
| 4,512,771 | 4/1985 | Norton | 604/324 |
| 4,561,858 | 12/1985 | Allen, Jr. et al. | 604/336 |
| 4,707,279 | 11/1987 | Walls | 251/339 |

FOREIGN PATENT DOCUMENTS

| | | | |
|---|---|---|---|
| 0576181 | 3/1946 | United Kingdom | 604/332 |
| 0663253 | 12/1951 | United Kingdom | 604/335 |
| 1212904 | 11/1970 | United Kingdom | 604/335 |
| 1363644 | 8/1974 | United Kingdom | 604/333 |

Primary Examiner—C. Fred Rosenbaum
Assistant Examiner—Mario Costantino
Attorney, Agent, or Firm—Senniger, Powers, Leavitt & Roedel

[57] ABSTRACT

A vented valve assembly for venting gas from a body collection pouch comprises structure for manually venting the gas from the pouch. The structure for manually venting the gas from the pouch include a housing, the walls of which define a chamber. The housing also includes an inlet and an outlet, the inlet adapted to be connected to the pouch. A valve for venting the gas from the pouch through the chamber from the inlet to the outlet is also provided which includes a valve seat located in the chamber adjacent the inlet, a valve stem extending in the chamber, a button attached to one end of the valve stem and extending out from the outlet, and a valve element attached to the other end of the valve stem and of a diameter smaller than that of the valve seat. The valve element being moveable between a closed position in close fit engagement with the valve seat and an open position remote from the valve seat upon the displacement of the button.

11 Claims, 3 Drawing Sheets

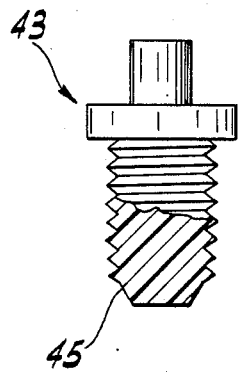
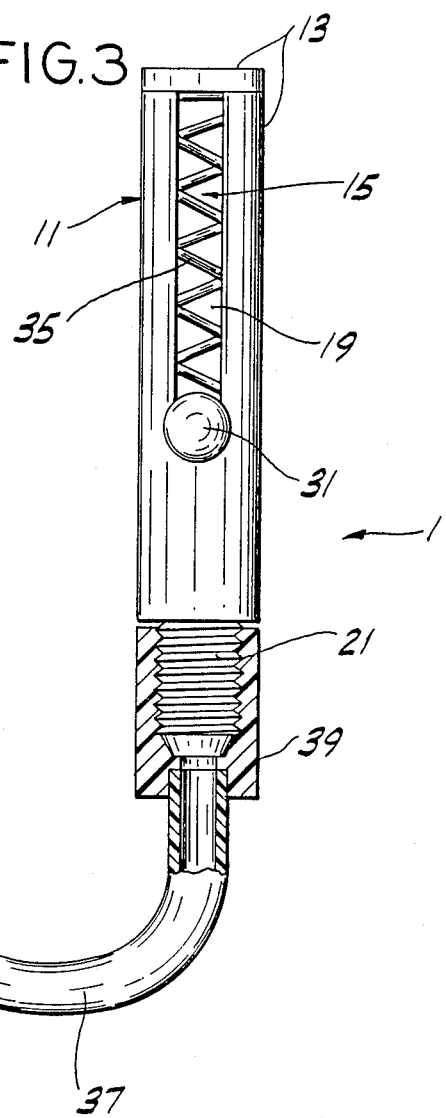
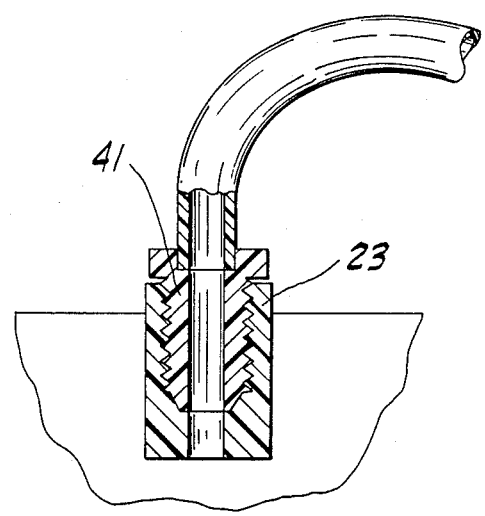

VALVED VENT ASSEMBLY FOR A BODY COLLECTION POUCH

BACKGROUND OF THE INVENTION

This invention relates to a valve assembly, and in particular to a valve assembly for venting gas from a body collection pouch.

Body collection pouches for use by ostomy patients are well known in the art and examples of such devices are disclosed in the following U.S. patents: Elmore et al., U.S. Pat. No. 3,865,109; Jensen et al., U.S. Pat. No. 4,411,659; and Allen, Jr. et al., U.S. Pat. No. 4,561,858. A problem associated with wearing a collection pouch is the venting of gas which accumulates in the pouch during use. When gas accumulates in the pouch it causes the pouch to expand resulting in the wearer's clothing becoming distorted. Some of the prior art devices have attempted to solve this problem by including gas venting means for removing the accumulated gas. However, these venting devices are subject to failure due to moisture or fecal matter blocking the vent.

Additionally, these prior art venting devices automatically vent gas from the pouch into the atmosphere. The pouch wearer has no control over the venting process. As is apparent, venting could occur at any time which is inconvenient and causes embarrassment to the wearer. Also, if any fecal matter escapes through the venting device, the wearer's clothing may become soiled and the wearer's skin may become irritated.

SUMMARY OF THE INVENTION

Among the objects of the present invention is the provision of a valve assembly for venting gas from a body collection pouch which is of simple construction for low cost and highly reliable operation; the provision of such a device that does not become clogged during operation; the provision of such a device that allows the pouch wearer full control over venting gas from the pouch; the provision of such a device may be reusable with other pouches; and the provision of such a device that may be positioned at a location remote from the pouch.

Briefly, a vented valve assembly of the present invention is for venting gas from a body collection pouch which comprises means for manually venting the gas from the pouch. The means for manually venting the gas from the pouch include a housing, the walls of which define a chamber. The housing also includes an inlet and an outlet, the inlet adapted to be connected to the pouch. A valve for venting the gas from the pouch through the chamber from the inlet to the outlet is also provided which includes a valve seat located in the chamber adjacent the inlet, a valve stem extending in the chamber, a button attached to one end of the valve stem and extending out from the outlet, and a valve element attached to the other end of the valve stem and of a diameter smaller than that of the valve seat. The valve element being moveable between a closed position in close fit engagement with the valve seat and an open position remote from the valve seat upon the displacement of the button.

Other objects and features will be in part apparent and in part pointed out hereinafter.

BRIEF DESCRIPTION OF THE DRAWINGS

FIG. 3 is a partial cross-sectional view of an extension for the vented valve assembly; and FIG. 4 is a partial cross-sectional view of a plug for the vented valve assembly.

Corresponding reference characters indicate corresponding parts throughout the several views of the drawings.

DETAILED DESCRIPTION OF THE PREFERRED EMBODIMENT

Figure 1:
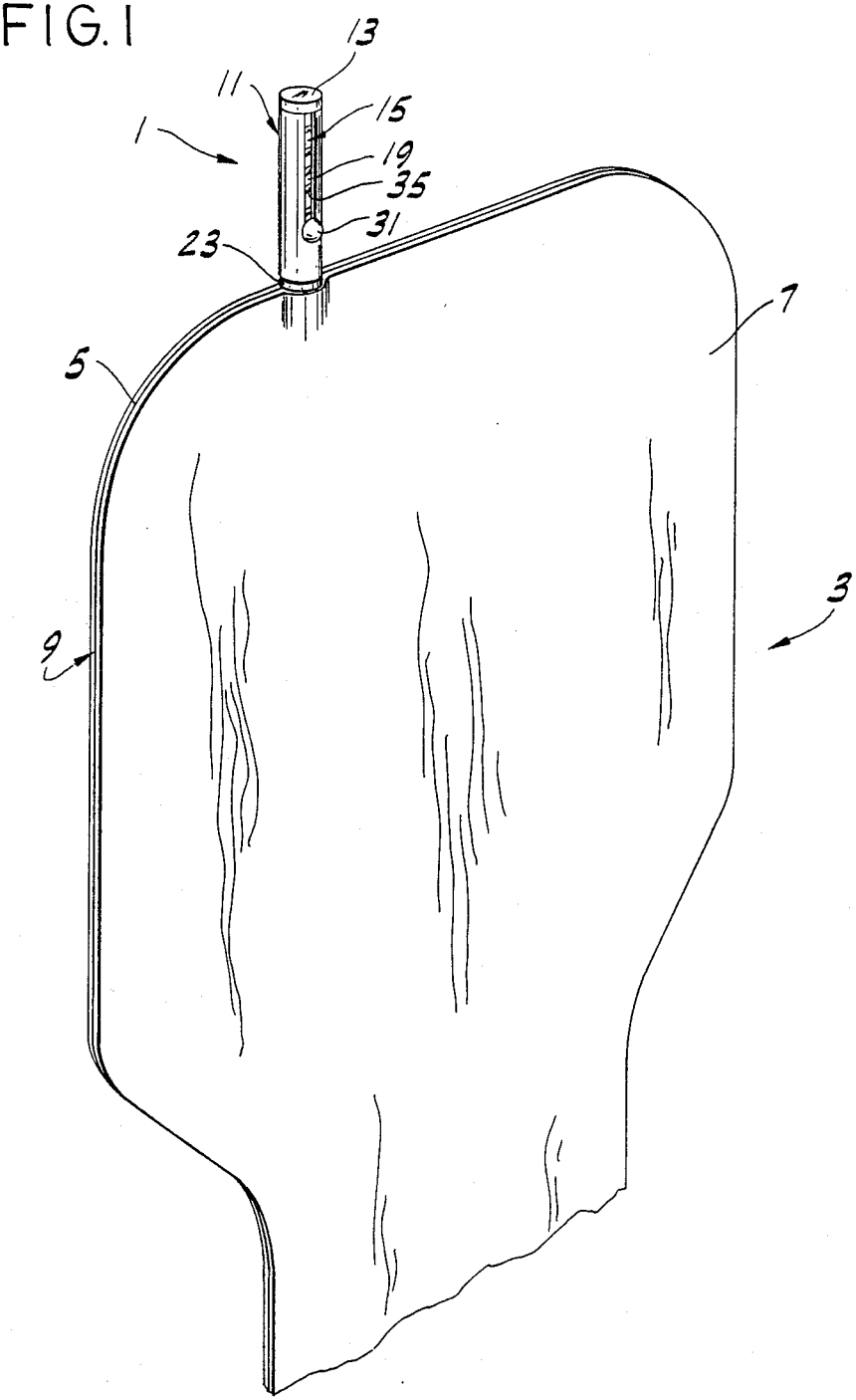
FIG. 1 is a perspective view of a vented valve assembly of the present invention connected to a body collection pouch.

The vented valve assembly of the present invention is indicated generally as 1 in the drawings. The body collection pouch is indicated generally as 3 in the drawings and may be formed in any of several well-known configurations. Typically, a body collection pouch is constructed from a relatively strong, soft moisture proof material such as transparent plastic material or polyethylene having a front wall 5 and a rear wall 7 which are heat sealed at their edges as indicated at 9. An opening (not shown) in the front wall 5 is provided to be attached to a stoma opening of a pouch wearer to receive fecal matter and gas from the wearer. The plastic material is usually very flexible to assume the wearer's body contours so as to conceal the pouch under the wearer's clothing.

The vented valve assembly 1, which is located at the top of pouch 3, comprises a generally cylindrical housing 11 having walls 13 which define a chamber 15. The housing 11 also includes an inlet 17 and an outlet 19. Inlet 17 is adapted to be connected to pouch 3 by a male connector 21 which extends from the inlet 17 of the housing 11 and which engages a female connector 23. Female connector 23 may be attached to pouch 3 by laminating it to the pouch 3 or by any other suitable method. Outlet 19 includes a slot formed in the wall 13 of the housing 11.

Figure 2:
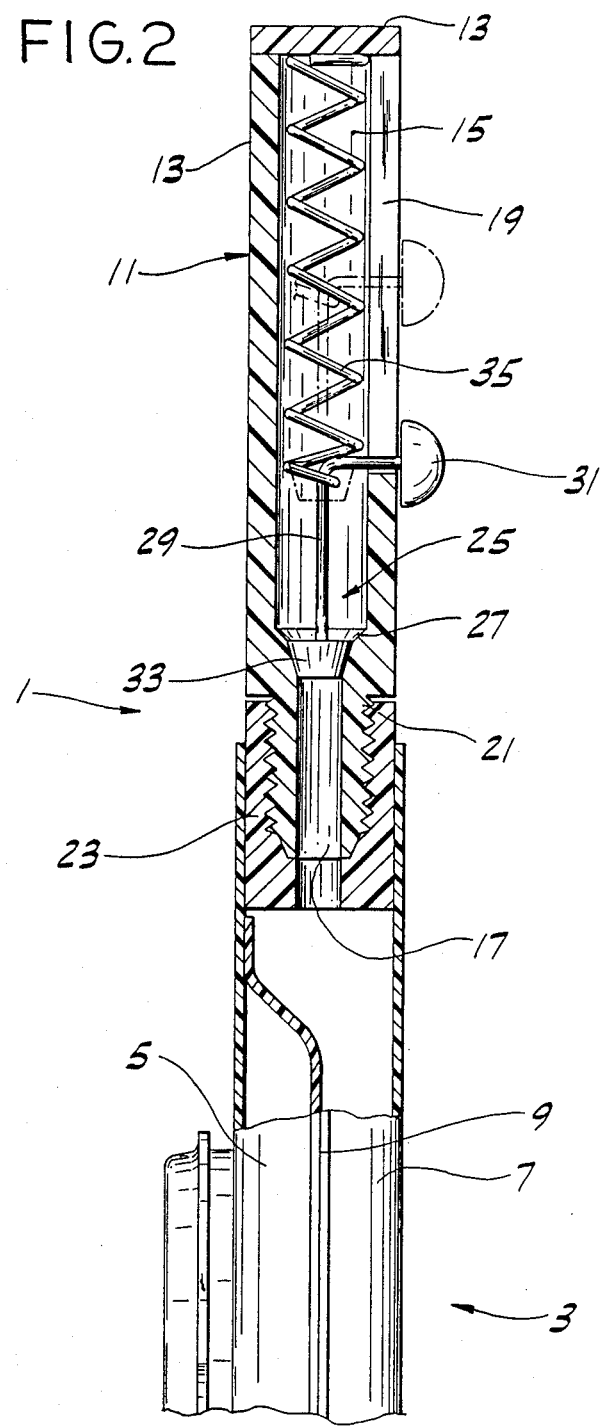
FIG. 2 is an enlarged cross-sectional view of the vented valve assembly of FIG. 1 with the button displaced in the open position shown in phantom.

A valve 25 is provided for venting gas from the pouch 3 through the chamber 15 from the inlet 17 to the outlet 19 into the atmosphere. The valve 25 includes a valve seat 27 adjacent inlet 17. A valve stem 29 extending in the chamber 15 has a button 31 attached to one end of the valve stem 29 which extends out from the housing 11 through outlet 19. A valve element 33 is attached to the other end of the valve stem 29. Valve element 33 has a diameter smaller than that of the valve seat 27 to act as a stopper or plug to establish a gas tight seal when valve element 33 is in contact with valve seat 27. Valve element 33 may be moved between a closed position in close fit engagement with valve seat 27 and an open position remote from the valve seat 27. Valve 25 also includes a spring 35 which is attached at one end to valve stem 29 and at the other end to housing 11. Movement from the closed position to the open position is accomplished by manually pushing button 31 against the bias created by spring 35 which displaces the valve element 33, valve stem 29, and button 31 away from the valve seat 27 as is illustrated in phantom in FIG. 2. Upon release of button 31, spring 35 forces valve element 33 back into engagement with the valve seat 27.

Referring to FIG. 3, an extension tube 37 with one end having a female connector 39 and the other end having a male connector 41 is shown connected at one end to male connector 21 and its other end connected to female connector 23. Since the stoma is not always located in the same position on each wearer, extension tube 37 is provided to enable the wearer to place vented valve assembly 1 at a location remote from pouch 3 in a position convenient and comfortable for the wearer. The extension tube 37 may be constructed from a flexible material. It is to be noted that male connectors 21 and 41 are of the same size to engage female connectors 23 and 39.

FIG. 4 illustrates a plug 43 which is adapted to be connected to female connector 23 when venting is not required such as during sleep or bathing. Plug 43 has a male end 45 which engages female connector 23 to prevent gas from escaping from pouch 3 when vented valve assembly 1 is not connected.

In use, the wearer manually pushes button 31 against the bias of spring 35 to remove valve element 33 from valve seat 27. Once removed, button 31 is held in place and gas in pouch 3 will escape through inlet 17 and chamber 15 where it will be expelled through outlet 19. When the gas has been eliminated, the wearer releases button 31 and spring 35 returns valve element 33 to engagement with valve seat 27.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed is:

1. A valve assembly for venting gas from a body fluid, gas, and matter collection pouch comprising means for detachably connecting the valve assembly to the pouch, means for manually venting the gas from the pouch connected to the detachably connecting means, the venting means comprising a housing, the walls of which define a chamber, the housing having an inlet and an outlet, a valve seat adjacent to the inlet, the inlet including means for connecting the housing to the pouch, a valve located within the housing for venting the gas from the pouch through the chamber from the inlet to the outlet, means for manually operating the valve, the valve comprises a valve stem extending in the chamber, a button attached to one end of the valve stem and extending out from the outlet, a valve element attached to the other end.of the valve stem and of a diameter smaller than that of the valve seat, the valve element being moveable within the chamber between a closed position in close fit engagement with the valve seat upon displacement of the button, and means for displacing the manually venting means away from the pouch.

2. The assembly of claim 1 wherein the valve further comprises means for biasing the valve in the closed position.

3. The assembly of claim 2 wherein the means for biasing the valve comprises a spring.

4. The assembly of claim 3 further comprising an extension tube removably connected to the valve assembly inlet, the extension tube having one end including means for connecting to the pouch and the other end including means for connecting to the inlet of the valve for placement of the manual venting means at a remote location from the pouch wherein upon displacement of the button the gas is vented from the pouch through the extension tube out the outlet.

5. In a body fluid, fecal matter, and gas collection device adapted for collecting fluid, fecal matter, and gas, the device comprising a closed pouch for receiving the fluid, fecal matter, and gas, the improvement comprising means for manually venting the gas from the pouch comprising a housing, the walls of which define a chamber, the housing having an inlet and an outlet, a valve seat adjacent to the inlet, the inlet including means for connecting the housing to the pouch, a valve located within the housing for venting the gas from the pouch through the chamber from the inlet to the outlet, means for manually operating the valve, the valve comprises a valve stem extending in the chamber, a button attached to one end of the valve stem and extending out from the outlet, a valve element attached to the other end of the valve stem and of a diameter smaller than that of the valve seat, the valve element being moveable within the chamber between a closed position in close fit engagement with the valve seat and an open position remote from the valve seat upon displacement of the button, means for detachably connecting the manually venting means to the pouch, and means for displacing the manually venting means away from the pouch.

6. The assembly of claim 5 wherein the valve further comprises means for biasing the valve in the closed position.

7. The assembly of claim 6 wherein the means for biasing the valve comprises a spring.

8. The assembly of claim 7 further comprising an extension tube removably connected to the valve assembly inlet, the extension tube having one end including means for connecting to the pouch and the other end including means for connecting to the inlet for placement of the manual venting means at a remote location from the pouch wherein upon displacement of the button the gas is vented from the pouch through the extension tube out the outlet.

9. A collection system comprising a pouch and a valve assembly, the valve assembly for venting gas from the body fluid, gas, and matter collection pouch, the pouch including a female connector, the valve assembly comprising:
  a housing detachably connected to the pouch, the walls of which define a chamber, the housing having an inlet and an outlet, the inlet including a valve seat located within the chamber and a male connector extending from the housing for connecting to the female connector; and
  a valve located within the housing for venting the gas from the pouch through the chamber from the inlet to the outlet, the valve including a valve stem extending in the chamber, a button attached to one end of the valve stem and extending out from the outlet, a valve element attached to the other end of the valve stem and of a diameter small than that of the valve seat, the valve element being moveable within the chamber between a closed position in close fit engagement with the valve seat and an open position remote from the valve seat and away from the pouch upon the displacement of the button.

10. The system of claim 9 further comprising an extension tube including means for detachably connecting one end to the female connector and means for connecting the other end to the male connector for placement of the assembly at a location remote from the pouch.

11. The system of claim 9 further comprising a plug adapted to be connected to the female connector for preventing gas from escaping from the pouch when the valve assembly is removed from the female connector.

* * * * *